Figure 1:
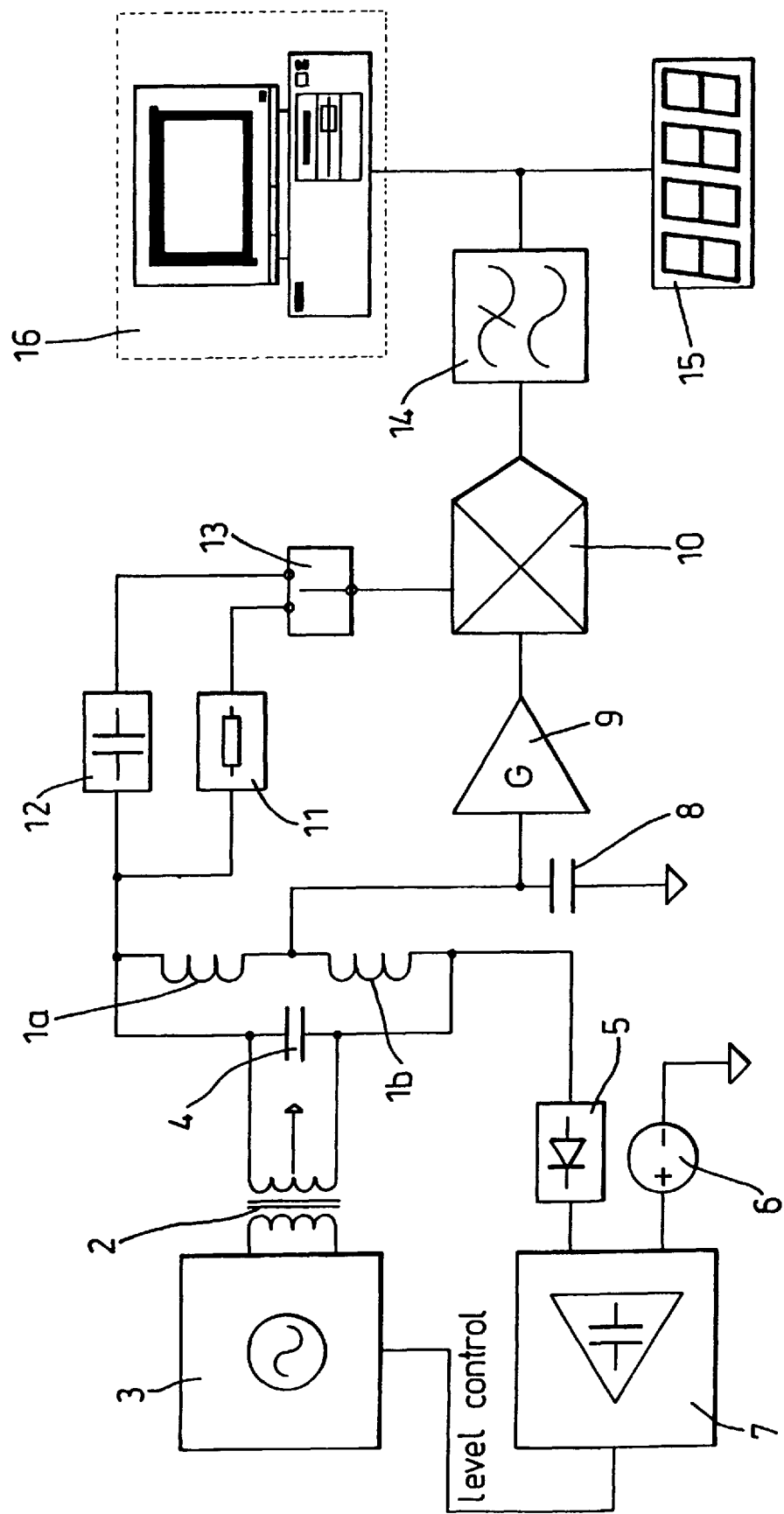

United States Patent
Hutchings

[11] Patent Number: 6,051,970
[45] Date of Patent: Apr. 18, 2000

[54] SYSTEM AND METHOD FOR MEASURING THE MAGNETIC CONDUCTIVE PROPERTIES OF A TEST FLUID

[76] Inventor: Michael John Hutchings, Manor Technology, 7 Oldenburg, Whiteley, Fareham, PO15 7EJ, United Kingdom

[21] Appl. No.: 09/049,775

[22] Filed: Mar. 27, 1998

[30] Foreign Application Priority Data

Apr. 1, 1997 [GB] United Kingdom .................... 9706554

[51] Int. Cl.[7] ........................... G01R 33/12; G01N 27/74
[52] U.S. Cl. ......................... 324/204; 73/61.42; 73/53.07
[58] Field of Search ................... 324/204, 228, 324/234, 236; 340/631; 73/61.42, 53.05, 53.07

[56] References Cited

U.S. PATENT DOCUMENTS

| 4,176,545 | 12/1979 | Oddo | 73/116 |
|---|---|---|---|
| 4,229,696 | 10/1980 | Gustafson | 324/204 |
| 5,404,100 | 4/1995 | Barnett et al. | 324/204 |
| 5,444,367 | 8/1995 | Kempster et al. | 324/204 |
| 5,506,501 | 4/1996 | Fogel et al. | 324/204 |
| 5,608,315 | 3/1997 | Crayton et al. | 324/204 |
| 5,811,664 | 9/1998 | Whittington et al. | 324/204 |

FOREIGN PATENT DOCUMENTS

| 107545 | 9/1983 | European Pat. Off. . |
|---|---|---|
| 2140568 | 4/1987 | United Kingdom . |
| 2269235 | 3/1996 | United Kingdom . |

OTHER PUBLICATIONS

D. A. Minnot and A. J. Parris on "Non–intrusive, low–frequency diagnostic of positive–glow plasma.", The institute of physics, vol. II, 1978 (No Date available).

*Primary Examiner*—Jay Patidar
*Attorney, Agent, or Firm*—Leydig, Voit & Mayer, Ltd.

[57] ABSTRACT

The magnetic or conductive properties of a test fluid, or of particles within a test fluid, are measured by an apparatus comprising a solenoidal coil (1a), a magnetic field carrying means (23) disposed radially outside the solenoidal coil, a tubular electrostatic screen (22) disposed radially within the solenoidal coil and radially outside a sample detecting volume, the test fluid being disposed in use within the sample detecting volume and separated radially from the innermost surface of the electrostatic screen by an air gap (18). The solenoidal coil is energised in use, and sensing means is provided for sensing the impedance of the solenoidal coil.

18 Claims, 4 Drawing Sheets

SYSTEM AND METHOD FOR MEASURING THE MAGNETIC CONDUCTIVE PROPERTIES OF A TEST FLUID

The present invention relates to apparatus to determine magnetic or conductive properties and is concerned particularly with measuring those properties of a fluid, suspension, solution, powder etc. by arranging a sample inside a magnetic field of a solenoidal coil, whose electrical impedance is monitored.

A second electrically similar coil can be used to compare the sample with properties of a reference sample, or as an electrical dummy. The apparatus is especially suited to measuring levels of the composite magnetic permeability and/or electrical conductivity of the sample. The permeability may be modified by the presence of wear generated ferromagnetic particles in hydraulic and lubricating fluids or of magnetic latex particles used in biochemical assays for example. The conductivity may vary due to the concentration of ions in a solution or presence of one or more electrically conductive, typically metallic particles for example. Both measurements are available at the same time and may be made on-line, in-line, or on a sample quantity, and comprise a sensitive contactless monitoring capability.

Much work is recorded in the literature directed at accurately monitoring fluid impedance by inductive means. Toroidal and solenoidal coils have both been employed, mainly in driven/sensing coil arrangements. We are not here concerned with toroidal coil systems (ie coils wound around toroidal soft magnetic formers) due to inherent insensitivity to permeability and their restricted application to conductive fluids only.

Minott and Parris (J Phys. E, 11 p 369, 1978), describe a rather complex six solenoidal coil method (2 driven, 2 sense, 2 balance), and introduce a grounded electro-static shield assembly to largely eliminate interfering dielectric effects. The electrostatic shield assembly comprises co-axial tubular shields located respectively radially inside and radially outside the three coils of each solenoidal coil assembly, and further circular shields extending across the opposite ends of each coil assembly. The dielectric effects can dominate in some circumstances if no shield is used.

EP A1107545 (Pharmuka Laboratories, France) details a test/reference solenoid method for determination of ionic concentration where the coils are separately resonated and driven in a form of bridge circuit. No mention is made of how balance is maintained as the operating environment changes.

In an American patent (U.S. Pat. No. 4,176,545, L Oddo) metallic wear debris in lubricant is collected on a filter placed inside a sensing coil and associated electronics detects the accumulation of particulate.

GB 2140568 (Pall Corporation) again addresses metallic debris detection in a filter using a differential transformer consisting of drive coil and two sense coils. Alternatively magnets may be used to accumulate the particles to achieve a useful sensitivity. There also exist several variant patent applications on a similar theme.

The accumulation approach does not require the high sensitivity demanded in the related field of detection of single debris particles. None of the foregoing methods have the sensitivity to detect 100 micron or less diameter particles which are considered to be of greatest interest in incipient failure detection. The present inventor is active in the field of single in-line particle detection and describes (in GB 2284891A) a two coil half bridge method with high sensitivity and discrimination between magnetic and conductive particles.

A U.S. patent (U.S. Pat. No. 5,444,367, assigned to Canadian Ministry of Defence) describes a single particle sensor system which uses two differential drive coils and a centrally placed pickup coil and employs electrostatic screening between coil and sample to avoid interfering dielectric effects. These two examples exhibit sensitivity to transient impedance changes due to particle passage.

The arrangement of the coils in an inductive detector is clearly of central importance. In all possible differential arrangements employing three coils, as either two drive and one sensing, or vice versa, the coils displaced along an axis as in U.S. Pat. No. 5,444,367, there will be a dominant part of the individual field coils which does not overlap with the dominant part of the next. It is in the overlapping region between two such coils with its necessarily lower field strength where the detectable interaction with the sample occurs, and so much potential sensitivity is lost. Use of driven sensing coils as in the present invention permits coil geometries which give optimal interaction of the particles with the sensor fields.

University College of Swansea in GB 2269235 claim a method of determining ferromagnetic particulate in liquid again based on differential transformer techniques. This is somewhat limited in sensitivity, quoted as being linear down to 100 ppm of ferrous material by volume, working as it does away from the point(s) of maximum field of the sensing coil(s).

The present invention provides a novel method and apparatus for monitoring of particulate bearing fluids but with single figure ppm sensitivity. The invention also has application to the measurement of the conductivity of materials, as for example ionic solutions in chemical titrations, or contamination of potable water, without the disadvantages pertaining to electrodes, such as fouling and poisoning.

According to a first aspect of the present invention there is provided apparatus for measuring the magnetic or conductive properties of a test fluid, or of particles within a test fluid, the apparatus comprising a solenoidal coil, a magnetic field carrying means disposed radially outside the solenoidal coil, a tubular electrostatic screen disposed radially within the solenoidal coil and radially outside a sample detecting volume, the arrangement being such that in use test fluid can be disposed within the sample detecting volume and is separated radially from the innermost surface of the electrostatic screen by an 'air gap', energising means for energising the solenoidal coil, and sensing means for sensing the impedance of the solenoidal coil.

The term 'fluid' is used herein to include a powder.

The term 'air gap' is used herein to include a vacuum space, or a space filled with a gas other than air.

The magnetic field carrying means is preferably of ferrite.

Preferably, the solenoidal coil is wound around the radially outer surface of a bobbin or former and the electrostatic screen is positioned on the radially inner surface of the bobbin or former, the screen being suitably earthed. The tubular screen could be other than circular in cross-section, and preferably the screen incorporates a break in its circumference so as to prevent circulating currents.

The screen may be constructed of a layer of graphite, or a film of a carbon-loaded plastics material, or of a polymer sheet coated with a flash of a suitable metal such as titanium, a wire mesh, or possibly a thin foil of a metal of relatively low electrical conductivity may be used.

The tubular screen preferably extends axially beyond both ends of the coil.

The magnetic field carrying means preferably extends axially beyond both ends of the coil.

The magnetic field carrying means preferably is of tubular shape, but one end may be closed by an integral end wall.

The field carrying means is preferably arranged to support the coil. Opposite ends of the coil bobbin or former are preferably attached to the innermost radial surface of the field carrying means.

Preferably the former or bobbin of the solenoidal coil is fixed to the tubular ferrite material by means of a resilient compound.

The tubular ferrite material is preferably fixed to the outer casing of the apparatus by a resilient compound.

Preferably the resilient compound is a silicone rubber in both cases.

The coil may comprise two or more axially spaced-apart series-connected portions if desired.

The coil is preferably a single-layer coil, but a plurality of layers may be employed if desired.

The apparatus is preferably provided with a non-conductive sample location tube coaxially disposed with respect to the coil, the arrangement being such that, in use, the outermost radial surface of the non-conductive sample location tube is separated from the innermost radial surface of the screen by the air gap.

Disposed coaxially around the circumference of the tubular ferrite material there is preferably a tubular outer metallic shield providing, in use, a barrier to external electromagnetic interference, the arrangement being such that external interference is substantially prevented from entering the detecting volume by the metallic shield.

The apparatus may comprise a tubular container within which the test fluid is contained in use. An annular spacer collar may then be disposed on the uppermost horizontal surface of the apparatus, with the upper end of the tubular container supported by the uppermost surface of the annular spacer, and the tubular container extending downwardly into the sample detecting volume, the arrangement being such that the base of the tubular container is disposed at substantially the centre of the detecting volume.

According to a second aspect of the present invention apparatus according to the first aspect of the invention is used for the detection of the conductivity of materials.

There is much value in certain applications in measuring electrical impedance without direct electrical contact. A considerable number of methods have been previously devised. Such non-invasive techniques are essentially magnetic, electric or electromagnetic field based. The present invention is concerned with interaction of the sample under evaluation with the magnetic field of one or more coils. The sample is placed inside an air cored solenoidal coil where substantially the maximum magnetic flux density occurs to provide greater sensitivity. As is well known the real part of coil impedance is modified by electromagnetic induction (eddy currents) causing dissipation in the sample. The imaginary part (inductance) is primarily influenced by changes in the reluctance of the path of magnetic flux through the sample. This responds to paramagnetic and diamagnetic material properties as well as the much stronger ferromagnetic and ferrimagnetic effects.

Although there may be significant electric field induction associated with the potential driving the solenoid current, only the magnetic field of the solenoid communicates with the sensing region in the present invention. Electric field coupling from coil to sensing region is preferably substantially avoided by incorporation of a carefully designed electrostatic screen between coil and sample, this screen consisting of an incomplete earthed layer of suitably conductive material. Spurious response to dielectric properties in the sample are thus substantially avoided. (Minute capacitive or 'displacement' currents induced in sample materials by the magnetic field give rise to concomitantly small changes in sensor coil 'inductance', but this undesired effect is usually too small to be of significance to measurement integrity.)

The smallest changes in coil impedance are enumerable by attention to choice of operating frequency, coil geometry and optimisation of the apparatus Q factor. One coil is associated with the sample under test and a second with a reference material to systematically compensate for common parametric changes of no interest. In many cases the reference coil may simply define an electrical baseline, and have no specific reference material applied. The coils are conveniently connected in an electrical bridge and are preferably driven by a ratio transformer or other balanced electronic means from an oscillator source. High stability of operation is very desirable both against time and temperature. Very stable oscillator, PSD (phase sensitive demodulator) and amplifier stages are desirable.

Advantageously coils are isolated from the sample by an air gas or vacuum filled break to help minimise mechanical stress from thermal coupling or other cause. The sample and reference coils are preferably operated isothermally, and a low thermal resistance path between them is desirable. To contain the external magnetic flux a ferrite sleeve is advantageously deployed outside the coil/s. This reduces the outside diameter of the sensor permitting a more compact and robust assembly. A metal outer layer in close proximity with the ferrite helps to maintain isothermal operation and provides additional screening from external electromagnetic sources.

The preferred embodiment of the present invention applies these features together for the first time in a practical apparatus with excellent sensitivity and discrimination, with good stability and electromagnetic compatibility.

Figure 2A:
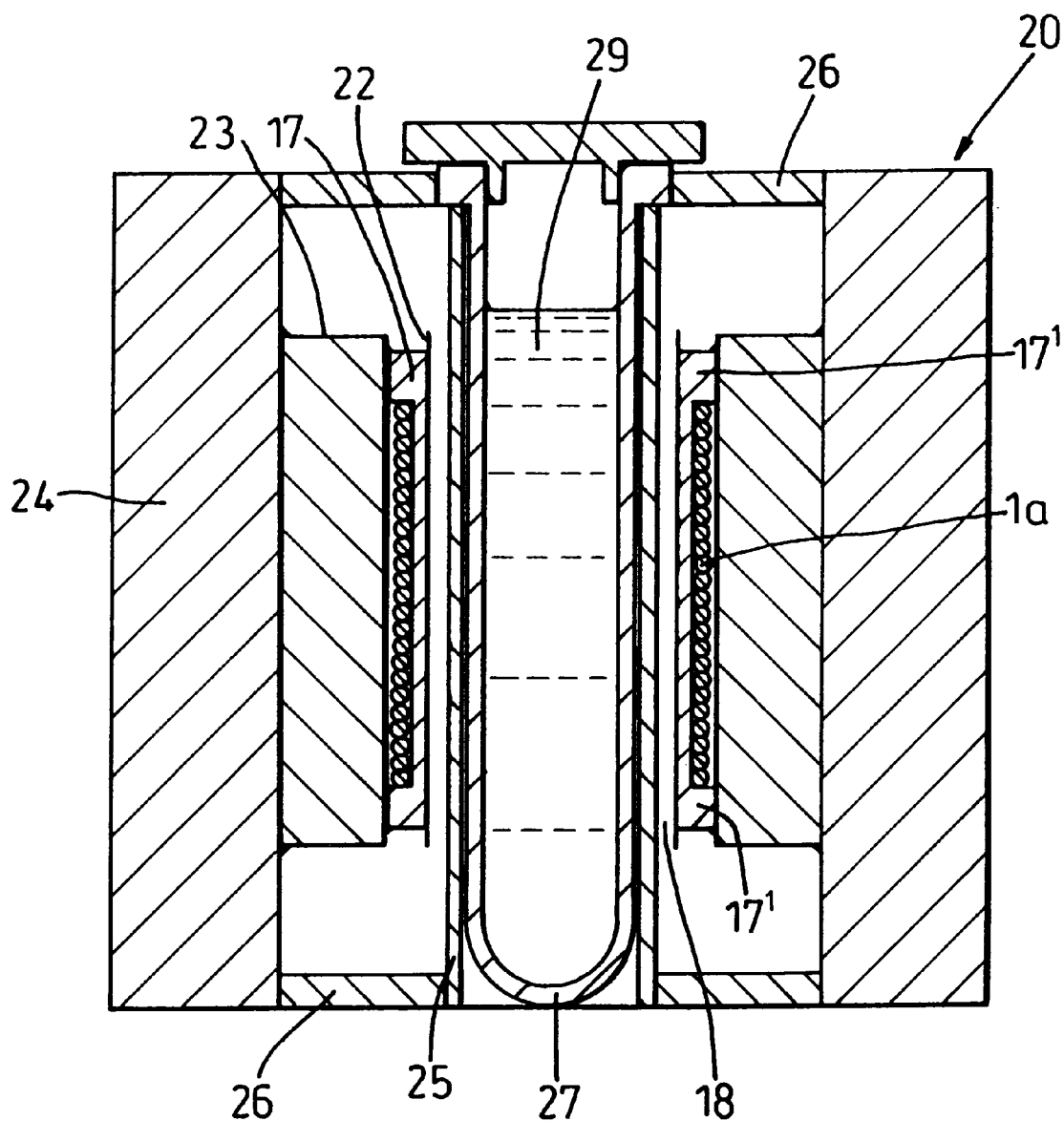
Figure 2B:
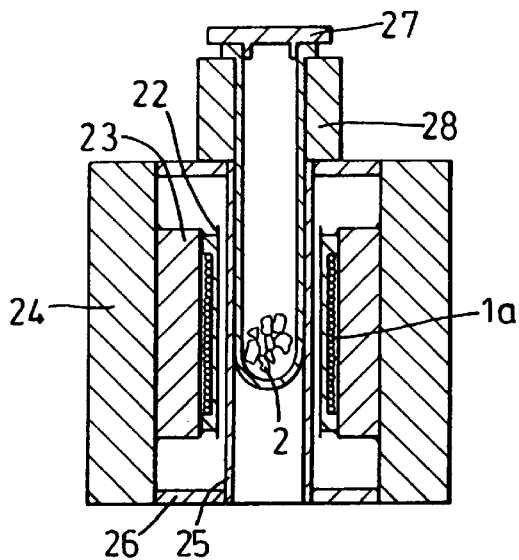
Figure 2E:
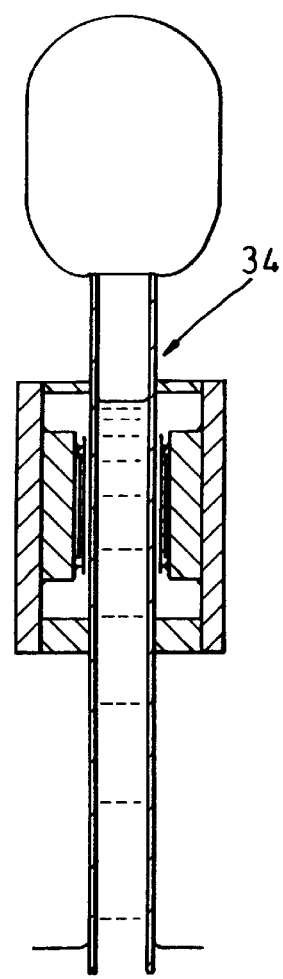
Figure 2C:
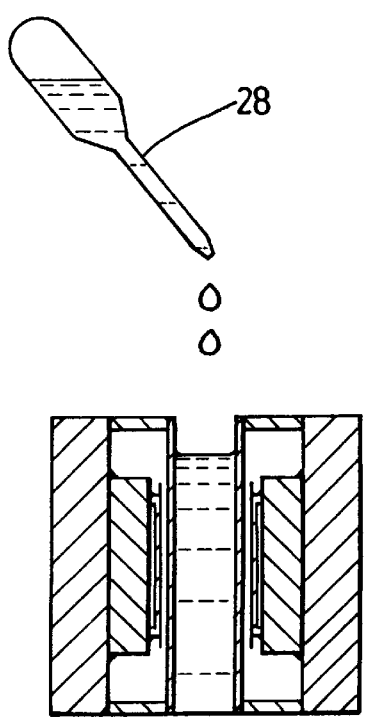
Figure 2D:
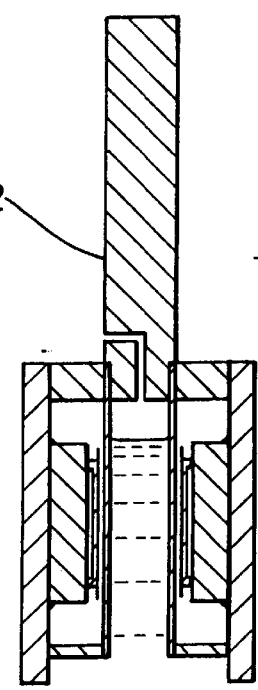
Figure 3:
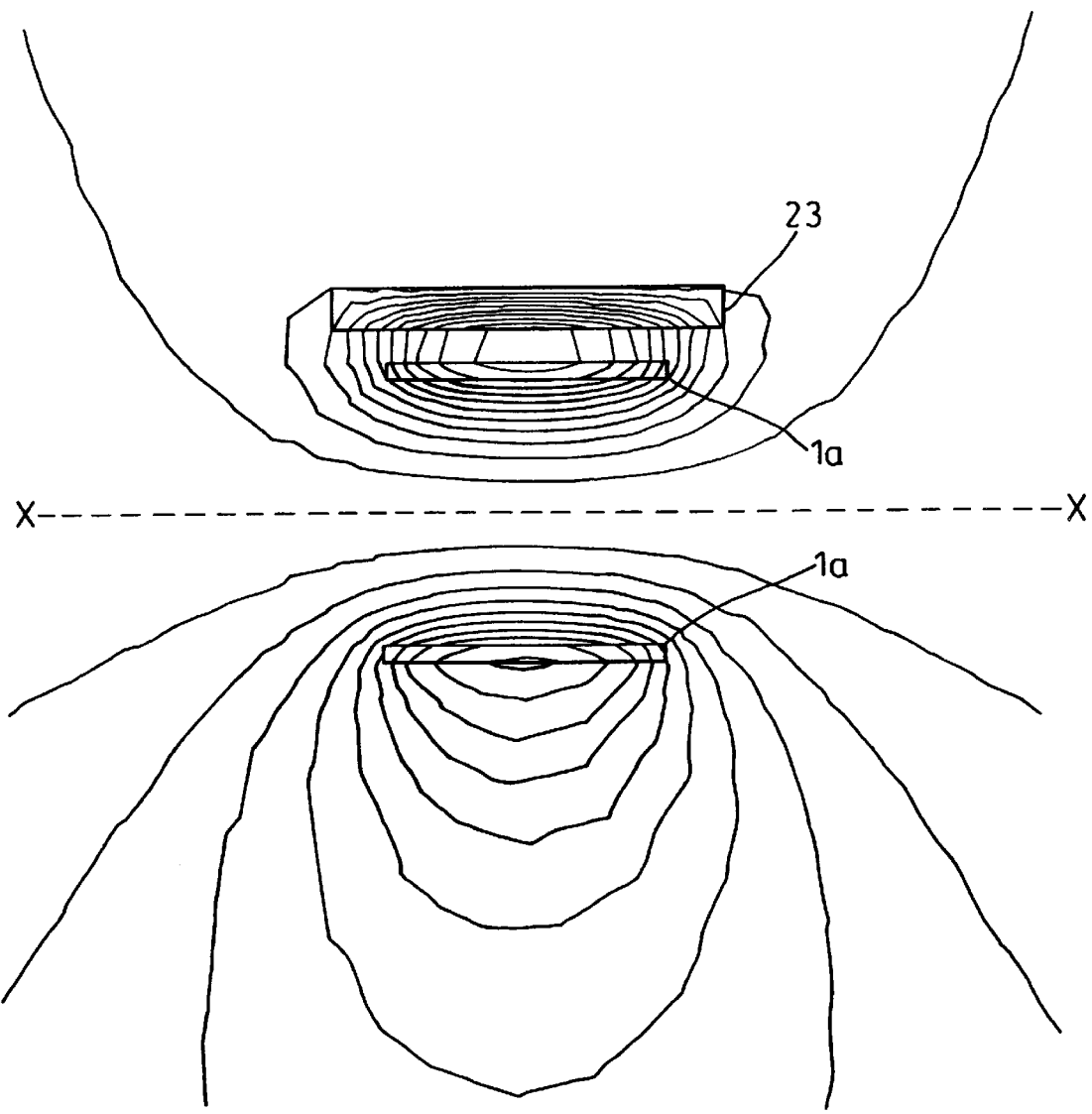

By way of example only various aspects of the present invention will now be described with reference to the accompanying drawings in which:

FIG. 1 is a block diagram of an impedance monitor incorporating detection apparatus in accordance with the invention, FIGS. 2a, 2b, 2c and 2d are diagrammatic vertical cross-sections of various apparatus all in accordance with the invention for the detection of particles within a test fluid, and FIG. 3 is a plot of the magnetic field of a coil with and without an external ferrite sleeve.

Referring to FIG. 1 the sensor coil 1a and reference coil 1b are arranged as a transformer 2 driven half bridge. An LC oscillator 3 uses the series coil impedance with a capacitor 4 connected in parallel as its frequency determining 'tank'. The oscillator circuit is preferably a balanced or push-pull type to reduce distortion levels and utilises low noise components where appropriate. To stabilise against temperature, ageing and other influences on amplitude the level of oscillation is ideally amplitude detected 5 and compared in an error integrator 7 with a stable reference voltage source 6, the output error signal providing negative feedback to a level control node at the oscillator. The frequency of oscillation may be locked to an external stable source e.g. a crystal oscillator if demanded by the particular application. The resonant drive of the coils reduces power consumption and wideband noise at the oscillator output and coil drive inputs. Note that the reference coil need not have the same absolute value as the sample coil provided that the transformer windings are scaled in the same ratio.

The frequency of the drive is chosen principally according to detail requirements of the measurement to be performed. If magnetic permeability is the only characteristic to be measured then a lower frequency of operation is indicated than where conductivity or conductive particles are of interest. The frequency choice is tempered by the need for coils of high Q factor with practical dimensions as well as circuit practicalities which make higher frequency operation generally more difficult and expensive. A typical operating frequency for magnetic permeability and conductivity dual sensitivities is 500 kHz.

A cross section of an exemplary sensor assembly 20 is shown in FIG. 2a. A single solenoidal coil 1a is wound around a tubular former 17, the radially inner surface of which supports a tubular electrostatic screen 22, the coil being mounted coaxially within a ferrite sleeve flux guide 23 by means of a resilient compound, eg silicone rubber, which secures the annular lands $17^1$ at opposite ends of the former to the radially inner surface of the flux guide 23.

As shown in FIG. 2a, the electrostatic screen 22 extends slightly above and below the extremities of the coil 1a, and the ferrite sleeve 23 also extends above and below the coil 1a.

The electrostatic screen may be a tubular wire mesh or a layer of an electrically conductive material such as graphite.

As a guide, the length:diameter of the sensing coil 1a is preferably within the range 1:1 to 2:1. The ferrite sleeve 23 is supported within an outer metallic block 24 by means of a layer of a resilient compound, eg silicone rubber extending over the confronting surfaces thereof.

The sample volume 29 inside the coil is defined by a suitable non-conductive tube 25 of, for example, acetal of greater length than coil 1a and sleeve 23, the tube 25 being supported at opposite ends thereof by end rings 26 attached to the outer block 24. This arrangement provides an air gap 18 between coil 1a and sample volume 29 which blocks heat transfer between a sample under test and the coil 1a and provides mechanical stress isolation.

A second similar assembly to assembly 20 may be used for the second bridge coil 1b to contain reference material if necessary for the measurement being made. In many applications, however, only an electrical dummy coil is required to provide coil 1b for initial bridge balance.

The measurement protocol may involve sequential measurement of reference and test samples in the same coil.

A fluid-bearing sample may be introduced into the sample volume 29 in a separate sample tube 27 as in FIG. 2a or directly, eg from a pipette 28 as in FIG. 2c into the interior of tube 25.

As shown in FIG. 2b, when a small solid sample or settled out particulate in fluid is introduced in a sample tube, the sample is constrained to be at the centre of the sensor coil by the use of an annular spacer collar 28.

Instead of placing a sample 2 in a sample tube 27, as in FIG. 2b, a dry sample 2 may conveniently be supported on adhesive tape on the end of a suitable holder, such as the open end of a glass tube.

In a modification, not illustrated, to the apparatus of FIG. 2b, the lower end of the ferrite sleeve 23 is closed by an integral ferrite base plate. Tube 25 is made of reduced length such that the lower end of tube 25 is spaced from said base plate. The base plate provides a reflection in the magnetic field pattern and facilitates the use of a shorter coil in circumstances where a longer coil is difficult to accommodate.

An immersible probe 32 modification of the assembly of FIG. 2a is shown diagramatically in FIG. 2d. A sample suction probe 34 modification is shown diagramatically in FIG. 2e.

In each fluid sample case the extent of the fluid sample should obviously best extend well beyond the coil ends to give sample volume independent reading(s).

Two coil assemblies similar to that shown in FIG. 2a may be used along a flow pipe in an on-line transient impedance detector (not shown).

FIG. 3 shows magnetic field lines for similar coils to the sensor coil 1a, with, above axis x—x, and, below axis x—x, without the external ferrite flux guide 23. The field pattern inside the solenoid, a radial cross-section only being shown, is not much changed, but the extent of the magnetic field outside is very much curtailed by the presence of ferrite guide 23. This significant addition of flux guide 23 permits much more compact assemblies and aids electromagnetic screening, as well as giving a useful increase of coil inductance due to the decreased reluctance of the magnetic circuit. The particular selection of ferrite material used is made by considering magnetic losses at the working frequency as well as attention to other material parameters such as Curie temperature and disaccommodation factor.

Returning to FIG. 1, to increase the output level for a given drive level the output reactance of the half bridge, that of the two coils 1a, 1b in parallel, is resonated with a suitable capacitive reactance 8 (or transformed to higher voltage/impedance level) and passed to a low noise amplifier 9 to allow the signal to noise ratio as limited by the Q of the coil to be preserved. Considering only thermal noise generated in the loss resistance of the coil, the signal to noise ratio is proportional to the square root of the Q factor of the coil. Any subsequent electronic stage will degrade this figure. Impedance transformation makes it possible to minimise this degradation. Overall 'sensitivity' is effectively a measure of the signal to noise ratio of the final system output. Provided the signal to noise ratio is adequate the output level can be varied arbitrarily. However useful sensitivity also depends on circuit drift and interference pick up amongst other things, and ensuring the lowest electronic noise may not bring proportional benefit.

With the bridge output signal boosted to appropriate level by the means of the measures taken in the previous paragraph it is fed to one or two phase sensitive demodulators (PSD) 10. Quadrature and in-phase reference inputs to the PSD's are provided by essentially reactive 12 and/or resistive 11 circuits. One PSD circuit 10 may be used with a switched reference as shown, employing a switch 13. The PSD must be highly stable at both the signal frequency and 'dc' output. A Gilbert cell mixer stage can be used but the input transistor pair should ideally be buffered and the tail current sources be similarly stabilised. Alternatively a switching type PSD or multiplier circuit may be employed, or the output digitised for the I/Q demodulation to be performed in the digital domain. Output stage(s) 14 deliver suitable amplification and remove unwanted high frequency components prior to display 15 or data logging employing for example a PC 16 as required. If only transient events are of interest as in on-line particle detection a band pass filter may be substituted at 14. Switchable phase references are disallowed in this case.

The sensor assemblies described above with reference to FIGS. 2a or 2b may be used in a number of modes. A sample may be introduced into a coil, in the form of a suspension of ferromagnetic particles in oil for example. A second, similar, reference coil assembly may have a sample of particle free oil inserted to null any effect of the oil from the static output reading.

In another mode a sample of solid ferromagnetic particles taken from for example a magnetic plug in an oil conduit may be placed inside a suitable container inside the sample coil. An empty container would provide the reference in such a case if required. For greatest sensitivity the sample holder tube 27 with the solid material assumed to be at its bottom is not inserted so far into the sensor as the position shown in FIG. 26. The same applies when solid particulate has settled out of the sample.

In a further mode of use one or two sensor assemblies may be placed in a flow stream to be monitored for conductivity or conductive or magnetic particulates. With two such assemblies the difference output gives indication of transient events such as particle passage. The average value of the two impedances in this case indicates the background level. One flow sensor with a reference mounted nearby to maintain a similar temperature can be used to measure the base level quantities for the flow stream. Alternatively coil temperatures may be monitored to allow for temperature stabilisation or the coil temperature to be actively controlled.

The tolerance to residual drift in the system output from whatever cause is much better in the external sampling case compared with the remote in or on-line installation intended to measure baseline values. Re-establishing the base-line level in the former case is possible before each sample. This may be manually adjusted or preferably be made automatically as a new sample is introduced. A data sampling subsystem then captures the transient change due to the sample after a preset delay for repeatable readings. This process may be controlled by an associated microprocessor which additionally supervises management of data logging and presentation, communication and temperature monitoring.

I claim:

1. Apparatus for measuring the magnetic or conductive properties of a test fluid, the apparatus comprising a solenoidal coil defining an interior space including a sample detecting volume, a magnetic field carrying means disposed radially outside the solenoidal coil, a tubular electrostatic screen disposed radially within the interior space defined by the solenoidal coil and radially outside the sample detecting volume such that test fluid can be disposed within the sample detecting volume and be separated radially from the innermost surface of the electrostatic screen by a gap, energizing means for energizing the solenoidal coil, and sensing means for sensing the impedance of the solenoidal coil.

2. Apparatus as claimed in claim 1 in which the solenoidal coil is wound around the radially outer surface of a bobbin and the electrostatic screen is positioned on the radially inner surface of the bobbin, the screen being adapted to be earthed in use.

3. Apparatus as claimed in claim 2 in which the field carrying means is arranged to support the coil.

4. Apparatus as claimed in claim 3 in which opposite ends of the coil bobbin are attached to the innermost radial surface of the field carrying means.

5. Apparatus as claimed in claim 3 in which the magnetic field carrying means is of tubular shape, and in which the bobbin of the solenoidal coil is fixed to the tubular magnetic field carrying means by means of a resilient compound.

6. Apparatus as claimed in claim 5 in which the resilient compound is a silicone rubber.

7. Apparatus as claimed in claim 1 in which the magnetic carrying means is constructed substantially of a ferrite material.

8. Apparatus as claimed in claim 1 in which the tubular screen extends axially beyond both ends of the coil.

9. Apparatus as claimed in claim 1 in which the magnetic field carrying means extends axially beyond both ends of the coil.

10. Apparatus as claimed in claim 1 in which the magnetic field carrying means is of tubular shape.

11. Apparatus as claimed in claim 1 in which the coil is a single-layer coil.

12. Apparatus as claimed in claim 1 provided with a non-conductive sample location tube coaxially disposed with respect to the coil, the arrangement being such that, in use, the outermost radial surface of the non-conductive sample location tube is separated from the innermost radial surface of the screen by the gap.

13. Apparatus as claimed in claim 1 further comprising a tubular outer metallic shield that surrounds the exterior of the solenoidal coil for providing a barrier to external electromagnetic interference such that the external interference is substantially prevented from entering the detecting volume by the metallic shield.

14. Apparatus as claimed in claim 1 wherein the detecting volume is further defined by a tubular container disposed within the interior space defined by the solenoidal coil.

15. Apparatus as claimed in claim 1 in which said gap contains air.

16. A method of measuring the magnetic or conductive property of a test fluid in a testing apparatus comprising a solenoidal coil defining an interior space including a sample detecting volume, a magnetic field carrying means disposed radially outside the solenoidal coil, a tubular electrostatic screen disposed radially within the interior space defined by the solenoidal coil and radially outside the sample detecting volume, energizing means for energizing the solenoidal coil, and sensing means for sensing the impedance of the solenoidal coil, the method comprising the steps of:

disposing the test fluid within the sample detecting volume such that the test fluid is separated radially from the innermost surface of the electrostatic screen by a gap;

energizing the solenoidal coil; and sensing the impedance of the solenoidal coil to determine the magnetic or conductive properties of the test fluid.

17. A method as claimed in claim 16 in which the fluid is a powder.

18. A method as claimed in claim 16 in which the fluid is a liquid containing a powder.

* * * * *